(12) United States Patent
Allison et al.

(10) Patent No.: US 7,266,176 B2
(45) Date of Patent: Sep. 4, 2007

(54) WORKSPACE OPTIMIZATION FOR RADIATION TREATMENT DELIVERY SYSTEM

(75) Inventors: John Allison, Los Altos, CA (US); John R. Dooley, Castro Valley, CA (US); Jay B. West, Mountain View, CA (US); Gopinath Kuduvalli, San Jose, CA (US); James Wang, Palo Alto, CA (US); Warren Kilby, Swinford Leics (GB); Derek Olender, San Jose, CA (US); Michael Saracen, Oakland, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

(21) Appl. No.: 11/237,007

(22) Filed: Sep. 28, 2005

(65) Prior Publication Data

US 2007/0071168 A1   Mar. 29, 2007

(51) Int. Cl.
*A61N 5/10* (2006.01)

(52) U.S. Cl. .......................................... 378/65; 378/205
(58) Field of Classification Search ............ 378/64–66, 378/207, 205, 108; 600/411, 427
See application file for complete search history.

(56) References Cited

U.S. PATENT DOCUMENTS 6,741,674 B2 * 5/2004 Lee .............................. 378/65

* cited by examiner

*Primary Examiner*—Hoon Song
(74) *Attorney, Agent, or Firm*—Blakely, Sokoloff, Taylor & Zafman LLP

(57) ABSTRACT

An apparatus and method for optimizing a workspace of a radiation treatment delivery system. An optimized treatment plan is generated for delivering a dose of radiation to a volume of interest ("VOI") in a patient using fewer changes to a treatment plan parameter during delivery of the dose of radiation then available to a radiation treatment delivery system. The optimized treatment plan limits a number of adjustments to the treatment plan parameter during delivery of the dose of radiation. Prior to delivery, the optimized treatment plan is analyzed to determine whether a quality of the optimized treatment plan is acceptable.

46 Claims, 7 Drawing Sheets

WORKSPACE OPTIMIZATION FOR RADIATION TREATMENT DELIVERY SYSTEM

TECHNICAL FIELD

This disclosure relates generally to the field of radiation treatment, and in particular but not exclusively, relates to optimizing radiation treatment delivery.

BACKGROUND

Tumors and lesions are types of pathological anatomies (e.g., tumors, lesions, vascular malformations, nerve disorders, etc.) characterized by abnormal growth of tissue resulting from the uncontrolled, progressive multiplication of cells that serve no physiological function. A non-invasive method for pathological anatomy treatment is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source is changed, every beam passes through the tumor site, but passes through a different area of healthy tissue on its way to the tumor. As a result, the cumulative radiation dose at the tumor is high and the average radiation dose to healthy tissue is low.

The term radiotherapy refers to a procedure in which radiation is applied to a target region or volume of interest ("VOI") for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (or fraction) (e.g., 100-200 centiGray (cGy)) and short treatment times (e.g., 10 to 30 minutes per fraction) over a period of days (e.g., 30 to 45 days of treatment). For convenience, the term "radiation treatment" is used herein to mean radiosurgery and/or radiotherapy unless otherwise noted by the magnitude of the radiation.

The two principal requirements for an effective radiation treatment system are homogeneity and conformality. Homogeneity is the uniformity of the radiation dose over the volume of the target (e.g., pathological anatomy such as a tumor, lesion, vascular malformation, etc.) characterized by a dose volume histogram ("DVH"). An ideal DVH for the pathological anatomy would usually be considered to be a rectangular function, where the dose is 100 percent of the prescribed dose over the entire volume of the pathological anatomy. An ideal DVH for a critical region (i.e., an important region or structure within the patient to avoid exposing to radiation) would have a rectangular function where the entire volume of the critical anatomical structures receives zero dose. In practice these ideal dose distributions are not achieved, and a range of dose is delivered to both the pathological and critical anatomical structures.

Conformality is the degree to which the radiation dose matches (conforms) to the shape and extent of the target VOI in order to avoid damage to critical adjacent structures. More specifically, conformality is a measure of the amount of prescription (Rx) dose (amount of dose applied) within a target VOI. Conformality may be measured using a conformality index (CI)=total volume at >=Rx dose/target volume at >=Rx dose. Perfect conformality results in a CI=1.

Treatment quality, which may be measured based on homogeneity, conformality, and risk of complications generally improves with the larger number of spatial nodes from which a radiation source can deliver the prescribed radiation dose. Providing a large number of spatial nodes enables the radiation source to have greater flexibility to irradiate the VOI from a larger sample of directions and angles, thereby increasing its ability to avoid critical structures while accurately delivering the prescribed dose to the target VOI. However, since radiation treatment systems typically use large, expensive equipment, the radiation source cycles through the entire set of spatial nodes along known safe interconnecting paths. Even though a particular treatment plan may call for delivery of radiation from only some of the available spatial nodes, the radiation source still visits each and every node along its known safe path to ensure a collision with the patient or other equipment does not occur.

Accordingly, the larger the number of spatial nodes the longer the treatment time. A smaller node set having fewer spatial nodes enables faster treatment time, but often at the expense of less flexibility and therefore potentially lower treatment quality. Accordingly, conventional techniques must balance treatment flexibility and quality versus treatment time.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Embodiments of a system and method for optimizing a workspace of a radiation treatment delivery system, for example, to reduce treatment times are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout this specification, several terms of art are used. These terms are to take on their ordinary meaning in the art from which they come, unless specifically defined herein or the context of their use would clearly suggest otherwise. The term "target" is defined herein as an anatomical feature(s) of a patient such as a pathological or normal anatomy, and may include one or more non-anatomical reference structures, at which a radiation source may target for radiation delivery.

Figure 1:
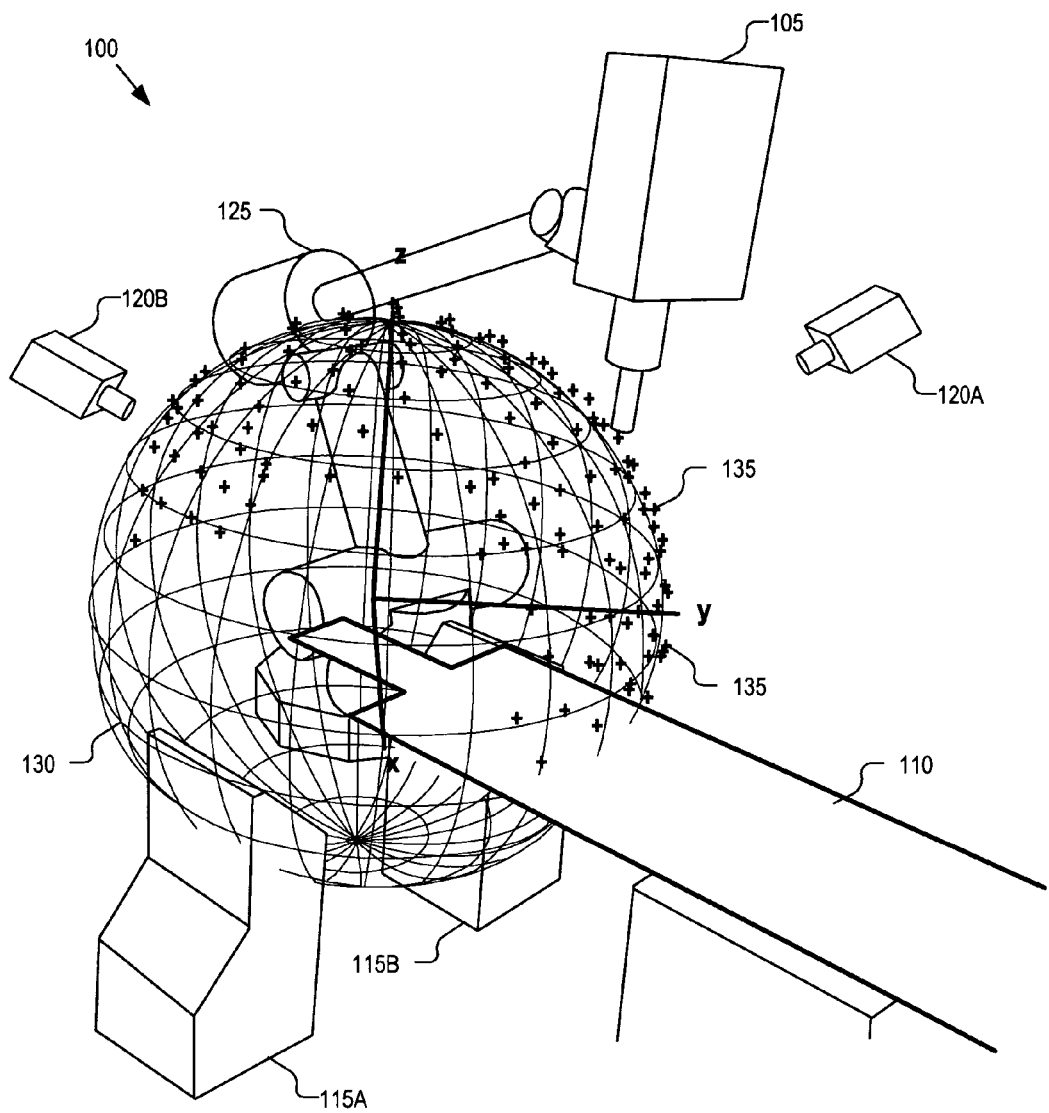
FIG. 1 is a perspective drawing illustrating a workspace of a radiation treatment delivery system including a set of spatial nodes at which to position the radiation source, in accordance with an embodiment of the invention.

FIG. 1 is a perspective drawing illustrating a workspace of a radiation treatment delivery system 100 including a set of spatial nodes at which to position the radiation source, in accordance with an embodiment of the invention. The illustrated embodiment of radiation treatment delivery system 100 includes a radiation source 105, a treatment couch 110, detectors 115A and 115B (collectively 115, also referred to as imagers), imaging sources 120A and 120B (collectively 120), and a robotic arm 125.

Radiation treatment delivery system 100 may be used to perform radiation treatment (e.g., radiosurgery and/or radiotherapy) to treat or destroy a lesion (e.g., tumorous tissue) within a patient. During radiation treatment, the patient rests on treatment couch 110, which is maneuvered to position a volume of interest ("VOI") containing a target to a preset position or within an operating range accessible to radiation source 105 (e.g., field of view). In one embodiment, radiation treatment delivery system 100 is an image guided radiation treatment delivery system. Together, imaging sources 120 and detectors 115 are an imaging guidance system that provides visual control over the position of treatment couch 110 and the patient thereon and the alignment of radiation source 105 with respect to the VOI within the patient. In one embodiment, treatment couch 110 may be coupled to a positioning system (not illustrated), such as a robotic arm, that receives feedback from the imaging guidance system to provide accurate control over both the displacement and orientation of the VOI within the patient relative to radiation source 105.

In one embodiment, robotic arm 125 has multiple (e.g., six) degrees of freedom capable of positioning radiation source 105 with almost an infinite number of possibilities within its operating envelope. Allowing this type of movement would result in several challenges. Firstly, a large number of positional possibilities creates a difficult problem to solve for a treatment planning system when determining beam positions and trajectories for treating a particular VOI. Secondly, allowing unconstrained movement within the operating envelope of robotic arm 125 may result in possible collisions between radiation source 105 and the patient or other stationary objects. These problems may be solved by limiting radiation source 105 to a finite number of spatial nodes from which radiation source 105 may emit a radiation beam and further creating specific paths (known safe paths) that robot arm 125 must follow between the spatial nodes.

A collection of spatial nodes and associated safe paths interconnecting these spatial nodes is called a "workspace" or "node set". FIG. 1 illustrates a workspace 130, including a number of spatial nodes 135 each represented by a "+" symbol (only a couple are labeled). Multiple different workspaces may be created and defined for different patient work areas. For example, workspace 130 may be spherical (as illustrated) and defined for treating VOIs residing within the head of a patient. Alternatively, workspace 130 may have other geometries (e.g., elliptical)and defined for treating VOIs residing within other areas of a patient. Additionally, multiple workspaces 130 may be defined for different portions of a patient, each having different radius or source to axis distances ("SAD"), such as 650 mm and 800 mm. The SAD is the distance between the collimator lens in radiation source 105 and the target within the VOI. The SAD defines the surface area of the workspace. In one embodiment of an elliptical workspace, the SAD may range from 900 mm to 1000 mm. Other SADs may be used.

Spatial nodes 135 reside on the surface of workspace 130. Spatial nodes 135 represent positions where radiation source 105 is allowed to stop and delivery a dose of radiation to the VOI within the patient. During delivery of a treatment plan, robotic arm 125 moves radiation source 105 to each and every spatial node 135 following a predefined path. Even if a particular treatment plan does not call for delivery of a dose of radiation from a particular spatial node 135, radiation source 105 will still visit that particular spatial node 135, since it falls along it predetermined safe path.

FIG. 1 illustrates a complete node set including an exemplary number of spatial nodes 135 (e.g., 100 to 115). The complete node set may include spatial nodes 135 substantially uniformly distributed over the geometric surface of workspace 130. The complete node set includes all programmed spatial nodes 135 and provides a workable number of spatial nodes 135 for effectively computing treatment plan solutions for most ailments and associated VOIs. The complete node set provides a reasonably large number of spatial nodes 135 such that homogeneity and conformality thresholds can be achieved for a large variety of different VOIs, while providing enough vantage points to avoid critical structures within patients. It should be appreciated that the complete node set may include more or less spatial nodes 135 than is illustrated or discussed. For example, as processing power increases and experience gained creating treatment plans, the average number of spatial nodes 135 may increase with time to provide greater flexibility and higher quality treatment plans.

Figure 2A:
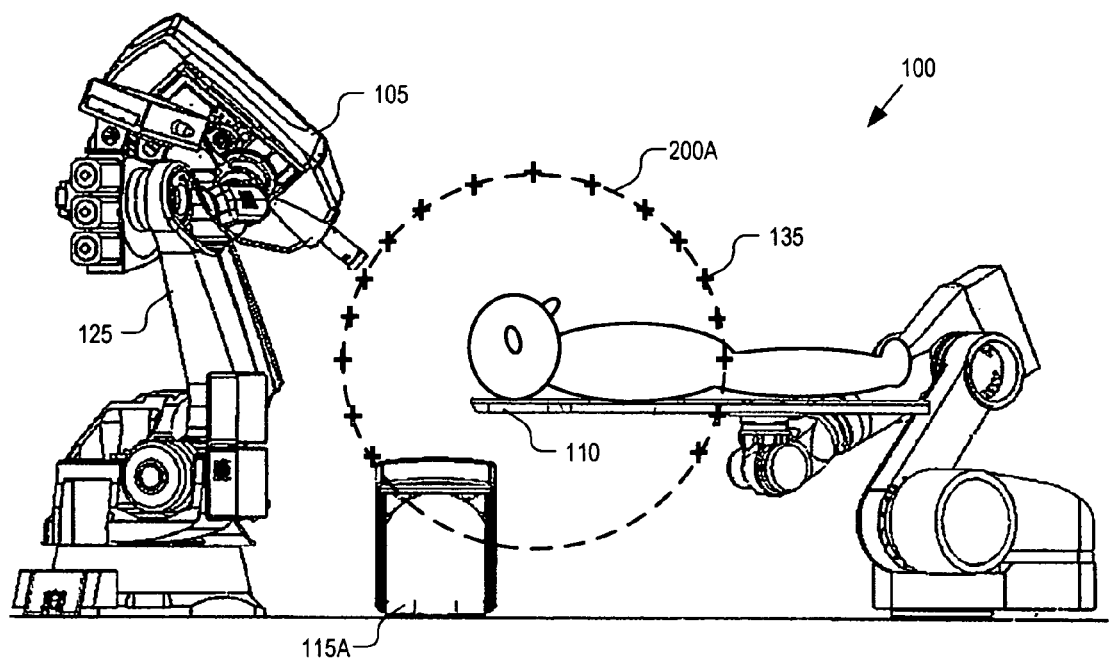
FIG. 2A is an elevational side view illustrating a cross-section of a workspace of a radiation treatment delivery system including a complete node set, in accordance with an embodiment of the invention.
Figure 2B:
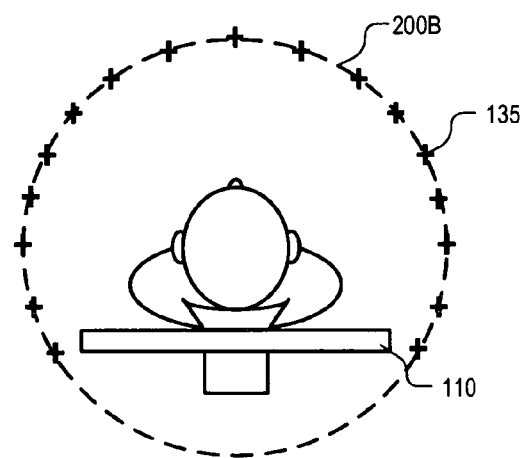
FIG. 2B is an elevational end view illustrating a cross-section of a workspace of a radiation treatment delivery system including a complete node set, in accordance with an embodiment of the invention.

FIG. 2A is an elevational side view and FIG. 2B is an elevational end view illustrating cross-sections 200A and 200B of workspace 130, in accordance with an embodiment of the invention. Cross-sections 200A and 200B illustrate how a complete node set of workspace 135 may have spatial nodes 135 evenly distributed around its surface. Other distributions are possible.

Using large or complete node sets of spatial nodes 135 increases flexibility to achieve conformality and homogeneity, while minimizing risk of complications to a patient for a wide variety of different VOIs. A larger node set provides a greater number of vantage points from which to delivery a radiation beam from radiation source 105. The greater the number of vantage points the greater the flexibility to design a treatment plan that avoids beam trajectories passing close to or through critical structures of a patient. Avoiding proximity to critical structures reduces the risks of complication to a patient.

However, the drawbacks of a large node set are increased complexity when calculating the treatment plan and lengthy delivery time for the treatment plan itself. In one embodiment, for safety considerations, radiation source 105 may be required to visit all spatial nodes 135 of workspace 130 during delivery of a treatment plan. If a treatment plan is calculated using 100 available spatial nodes 135, then radiation source 105 visits all 100 spatial nodes 135 during delivery of the treatment plan, even if the treatment plan only calls for a dose of radiation to be delivered from 30 of the 100 spatial nodes 135. Therefore, increasing the number of spatial nodes 135 increases treatment flexibility at the expense of treatment delivery time.

FIGS. 2A and 2B illustrate workspaces using complete node sets for calculating and generating complete node treatment plans. A complete node set is a set of spatial nodes 135 that includes all available spatial nodes 135. A complete node treatment plan is a treatment plan that has been calculated and generated based on a complete node set programmed into radiation treatment delivery system 100. However, a complete node treatment plan need not call for radiation to be delivered at all spatial nodes 135 of a complete node set; rather, radiation source 105 merely visits all spatial nodes 135 programmed into radiation treatment delivery system 100.

Figure 3A:
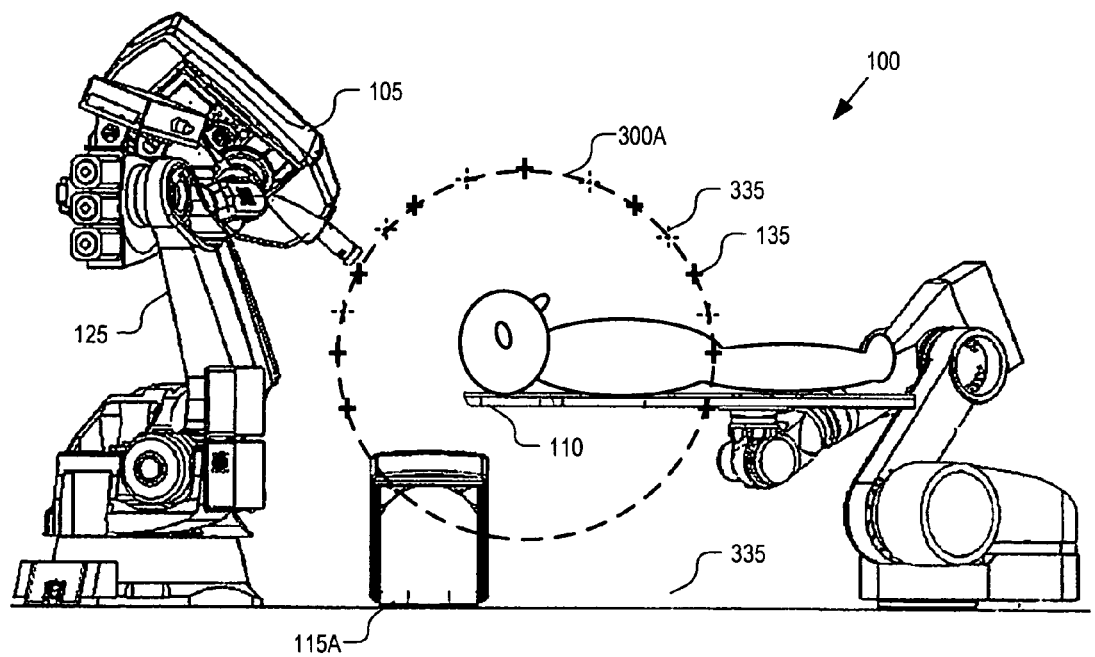
FIG. 3A is an elevational side view illustrating a cross-section of a workspace of a radiation treatment delivery system including a partial node set, in accordance with an embodiment of the invention.
Figure 3B:
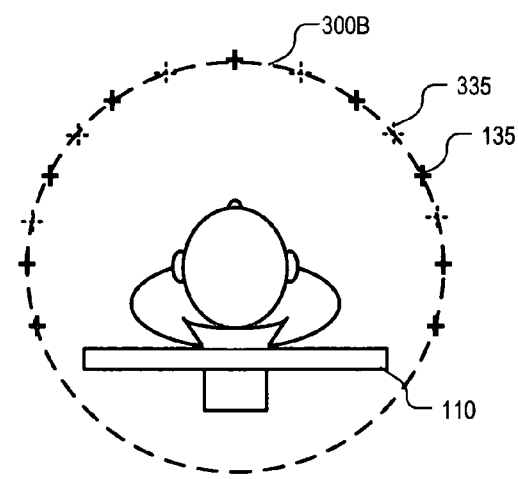
FIG. 3B is an elevational end view illustrating a cross-section of a workspace of a radiation treatment delivery system including a partial node set, in accordance with an embodiment of the invention.

FIG. 3A is an elevational side view and FIG. 3B is an elevational end view illustrating cross-sections 300A and 300B of a reduced node workspace, in accordance with an embodiment of the invention. The reduced node workspace includes a node subset for calculating/generating partial node treatment plans. FIGS. 3A and 3B illustrate the unused spatial nodes 335 as dashed "+". Unused spatial nodes 335 represent spatial nodes 135 of the complete node set illustrated in FIGS. 2A and 2B that are unused with a particular node subset.

A partial node treatment plan is a treatment plan calculated/generated using only a portion or subset of the available spatial nodes programmed into radiation treatment delivery system 100. For example, a node subset may include only 50 of an available 100 spatial nodes 135. Spatial nodes 135 of a node subset are also interconnected by known safe paths for moving radiation source 105 between spatial nodes 135 of the node subset. Accordingly, if a partial node treatment plan calls for radiation to be delivered from 20 spatial nodes of 50 total spatial nodes defined by a node subset, radiation source 105 still visits all 50 spatial nodes during treatment delivery. However, it should be appreciated that radiation source 105 will not visit the available spatial nodes 135 excluded from the node subset (i.e., unused spatial nodes 335). Therefore, partial node treatment plan delivery times are reduced due to the node subsets.

In one embodiment, the node subset may be a sparse, evenly distributed, version of the complete node set that includes total angular coverage with less density. In one embodiment, the node subset may be similar to the complete node set, but excluding the least frequently used spatial nodes 135. In one embodiment, the node subset may include spatial nodes 135 which empirical evidence has shown to be routinely used to treat a particular ailment or type of VOI. For example, the node subset may include those spatial nodes 135 commonly used for treating prostate lesions, breast lesions, spinal lesions, lung lesions, or other types of tumorous lesions. Accordingly, node subsets may be created for targeting anatomy features. Various other node subsets may be created based on prior planning experience and treatment site characteristics.

Constraining radiation source 105 to a fewer number of spatial nodes 135 (e.g., node subset) decreases delivery time of a partial node treatment plan when compared to the complete node treatment plan. By generating a variety of node subsets and storing these in a library for use to generate partial node treatment plans the flexibility provided by a complete node set is retained. As the number of spatial nodes 135 in a complete node set increases to provide more flexible and higher quality treatment plans, treatment times need not increase proportionally. Maintaining a database of node subsets enables selection of a node subset which is well suited for a particular VOI and/or patient that retains treatment quality while reducing treatment time. Embodiments of the present inventions may ameliorate the tradeoff between treatment quality and treatment time that may be inherent in a one size fits all approach.

Node subsets may be used to optimize a variety of other factors than just reducing treatment time. Furthermore, optimized treatment plans may be optimized for other treatment planning parameters. For example, other treatment planning parameters that could be optimized include total number of imaging centers per treatment plan, total number of treatment couch 110 positions per treatment plan, or reducing the SAD of a given treatment plan, as wells as other treatment planning parameters.

An imaging center of radiation treatment delivery system 100 is the focal center of imaging sources 120 for a given position. The imaging center represents the field of view of imaging sources 120 in a given position and dictates the operating envelope of radiation source 105 for the given position of imaging sources 120. If a treatment plan calls for multiple imaging centers, imaging sources 120 are repositioned to focus on a new imaging center. Changing an imaging center may include not only repositioning imaging sources 120, but also repositioning radiation source 105 and/or treatment couch 110 based on the new imaging center, as wells as, re-executing alignment and registration procedures. Optimizing a treatment plan to reduce the total number of imaging centers includes determining whether alternative treatment plans exist that use fewer imaging centers, but still achieve acceptable treatment results.

If a treatment plan calls for multiple positions of treatment couch 110, then treatment couch 110 is repositioned two or more times during delivery of the single treatment plan. Changing a position of the treatment couch 110 may include not only repositioning treatment couch 110, but also repositioning radiation source 105 and/or imaging sources 120 based on the new treatment couch 110 position, as wells as, re-executing alignment and registration procedures. Optimizing a treatment plan to reduce the total number of treatment couch 110 positions includes determining whether alternative treatment plans exist that use fewer positions of treatment couch 110, but still achieve acceptable treatment results. A treatment plan may call for multiple positions of treatment couch 110 to access the VOI from different approach angles, due to physical constraints (e.g., equipment and room geometries), or the like.

If a treatment plan calls for multiple SAD of radiation source 105, then radiation source 105 is repositioned onto a different workspace having a different surface contour two or more times during delivery of the single treatment plan. Changing workspaces may include not only repositioning radiation source 105, but also repositioning treatment couch 110 and/or imaging sources 120 based on the new SAD, as wells as, re-executing alignment and registration procedures. Optimizing a treatment plan to reduce the total number of SADs includes determining whether alternative treatment plans exist that use fewer SADs, but still achieve acceptable treatment results.

Figure 4:
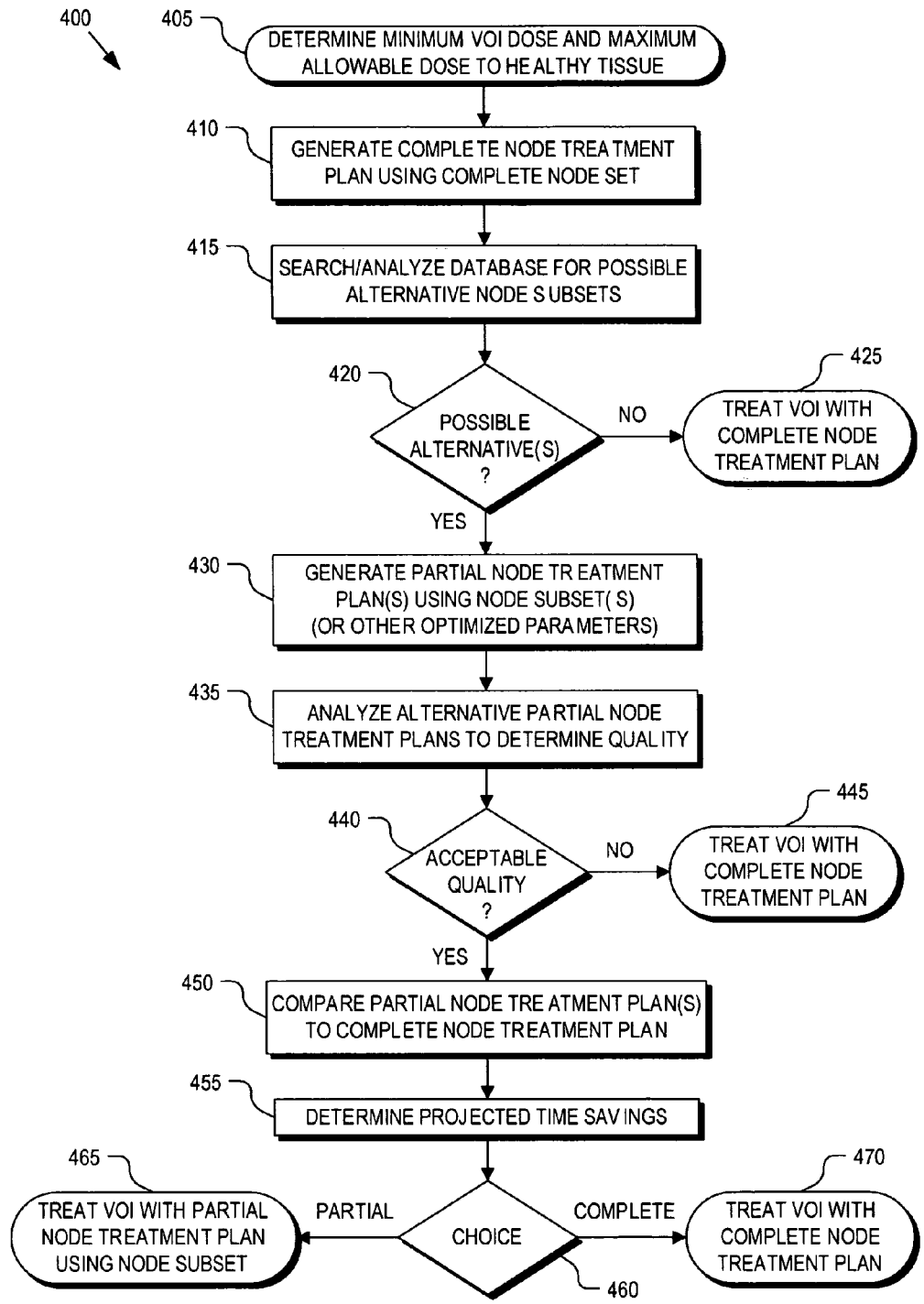
FIG. 4 is a flow chart illustrating a process for optimizing a workspace of a radiation treatment delivery system to reduce treatment time, in accordance with an embodiment of the invention.

FIG. 4 is a flow chart illustrating a process 400 for optimizing the workspace of radiation treatment delivery system 100, in accordance with an embodiment of the invention. The techniques described may constitute machine-executable instructions embodied within a machine readable medium, that when executed by a machine will cause the machine to perform the operations described. Additionally, process 400 may be embodied within hardware, such as an application specific integrated circuit ("ASIC") or the like. The order in which some or all of the process blocks appear in process 400 should not be deemed limiting. Rather, one of ordinary skill in the art having the benefit of the present disclosure will understand that some of the process blocks may be executed in a variety of orders not illustrated.

In a process block 405, a medical physicist or radiation oncologist specifies the minimum dose to be delivered to the VOI (e.g., prescribed dose of radiation) and the maximum acceptable dose to other healthy tissue surrounding the VOI. In a process block 410, the minimum VOI dose and maximum healthy tissue dose are input into treatment planning software that automatically calculates a treatment plan. The treatment planning software determines the directions, SAD(s), treatment couch position(s), imaging center(s), and the total number and energy of the beams used to delivery the prescribed dose of radiation to the VOI. This technique of treatment planning is referred to as "inverse planning."

In process block 410, the treatment planning software generates a complete node treatment plan using the complete node set illustrated in FIGS. 1, 2A, and 2B. The treatment planning software produces the treatment plan, relying on the positional capabilities of radiation treatment delivery system 100 constrained by the complete node set, to meet the min/max dose prescription constraints. The complete node set allows the treatment planning software to use all available spatial nodes 135 from which to delivery the prescribed dose of radiation. Of course, the complete node treatment plan prescribes that radiation source 105 will visit all spatial nodes 135 made available to the treatment planning software during calculation/generating of the complete node treatment plan. Accordingly, the complete node treatment plan may represent the highest quality treatment plan attainable by radiation treatment delivery system 100, but also represents the slowest treatment delivery time.

In a process block 415, a database is searched to determine whether any node subsets exist that may be possible alternatives to the complete node set used. In one embodiment, the database may store node subsets indexed to anatomy features (e.g., spinal lesions, prostate lesions, breast lesions, lung lesion, etc.). In this embodiment, searching the database may simply include querying the database to determine whether optimized node subsets for treating the particular ailment or anatomical structure have been stored.

In other embodiments, searching the database of node subsets may include analyzing the complete node treatment plan to determine which spatial nodes 135 are actually used to delivery the prescribed dose of radiation. Then, the database may be searched to determine whether any node subsets exists which includes all or a majority of the spatial nodes 135 used by the complete node treatment plan, but also exclude unused spatial nodes 335. In one embodiment, the searching/analysis algorithm may search for node subsets that include the particular spatial nodes 135 designated to receive the largest doses, while being willing to tradeoff spatial nodes 135 designated to deliver low doses. The database may be queried to determine if other treatment plan parameters may be optimized including total number of imaging centers, total number of couch positions, total number of SADs, and the like.

If no possible (or reasonable) alternative exists (decision block 420), then the complete node treatment plan calculated in process block 410 is used to treat the VOI (process block 425). However, if the preliminary search/analysis of the database suggests that one or more of the node subsets may be possible alternatives to the complete node set (decision block 420), then process 400 continues to a process block 430.

In process block 430, the treatment planning software generates partial node treatment plans using the node subsets determined in process block 415. The treatment planning software produces the partial node treatment plans, relying on the positional capabilities of radiation treatment delivery system 100 constrained by the node subsets, to meet the min/max dose prescription constraints. In process block 430, the treatment planning software may also generate other optimized treatment plans using fewer imaging centers, treatment couch 110 positions, SADs, and the like.

In a process block 435, the partial node treatment plans (or other optimized treatment plans) are then analyzed to determine their quality. As discussed above, quality of a treatment plan may be characterized based on its conformality to the VOI, its homogeneity over the VOI, and its risk of complications to the patient, while achieving the min/max dose constraints.

If all of the partial node treatment plans are determined to be of insufficient quality to treat the patient (decision block 440), then the prescribed dose of radiation is delivered to the VOI using the complete node treatment (process block 445). However, if one or more of the partial node treatment plans is determined to be of sufficient quality within an acceptable deviation, then process 400 continues to a process block 450.

In process block 450, metrics between the partial node treatment plans (or other optimized treatment plans) and the complete node treatment plan are compared. These metrics may include conformality, homogeneity, and risk of complications. In a process clock 455, the projected time saving of the partial node treatment plans over the complete node treatment plan is also determined. With reference to the projected time savings and the metrics comparisons (e.g., quality deviation), it is determined in decision block 460 whether one of the partial node treatment plans should be used to deliver the prescribed dose (process block 465) or whether the complete node treatment plan should be used (process block 470). The choice whether to use one of the partial node treatment plans or the complete node treatment plan may be made by the medical physicist or radiation oncologist, the operator of the radiation treatment delivery system 100, or even by software according to defined rules. The choice whether to use one of the partial node treatment plans or the complete node treatment plan may require balancing the projected times savings versus the quality deviation. If the treatment time savings are substantial and the quality deviation is small, then the partial node treatment plan using one of the node subsets may be a desirable alternative. If however, the time savings are minimal or the quality deviation is substantial, then the complete node treatment plan may be selected. A similar balancing algorithm or process is applied when determining whether to use other optimized treatment plans over the complete node treatment plan.

Figure 5:
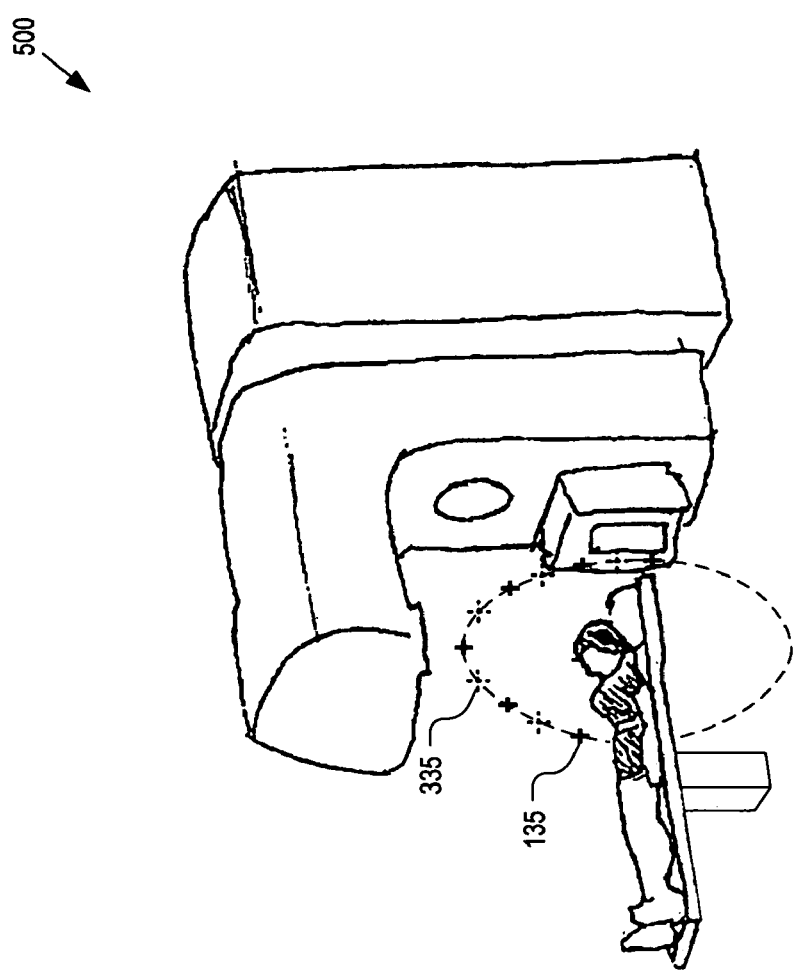
FIG. 5 illustrates how techniques described herein may be implemented using a gantry based radiation treatment delivery system, in accordance with an embodiment of the invention.

FIG. 5 illustrates how the techniques described herein may be implemented in connection with a gantry based radiation treatment delivery system 500, in accordance with an embodiment of the invention. As illustrated, complete node treatment plans for use with gantry based radiation treatment delivery system 500 may be optimized by reducing the number of spatial nodes 135 by eliminating unused spatial nodes 335, as discussed above. If a particular complete treatment plan calls for multiple treatment couch positions of gantry based radiation treatment delivery system 500, then the techniques herein may be used to reduce the number of treatment couch positions.

Figure 6:
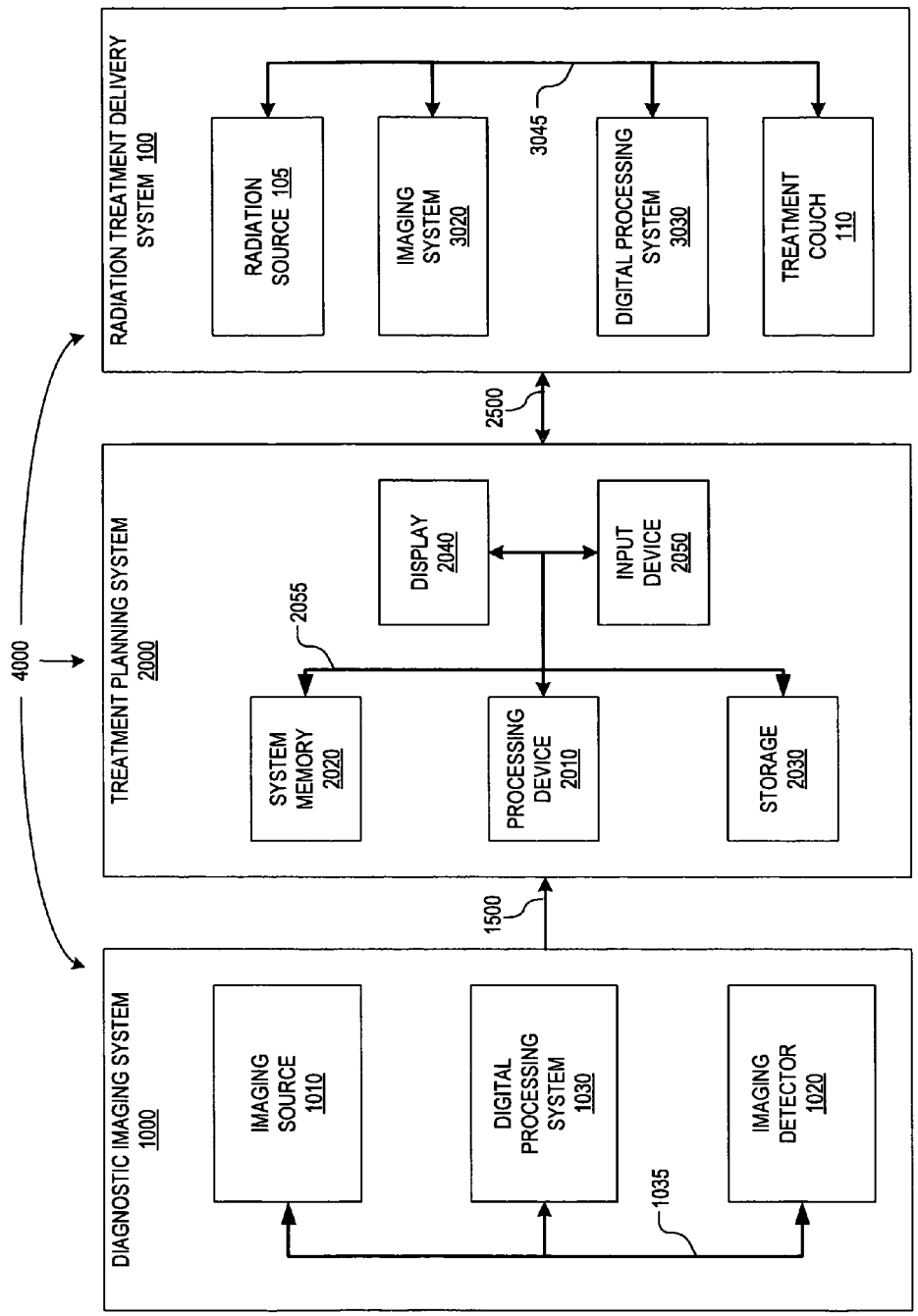
FIG. 6 is a block diagram illustrating a patient treatment system for generating diagnostic images, generating a treatment plan, and delivering the treatment plan, in accordance with an embodiment of the invention.

FIG. 6 is a block diagram illustrating a patient treatment system 4000 for generating diagnostic images, generating a treatment plan, and delivering the treatment plan to a patient, in which features of the present invention may be implemented. As described below and illustrated in FIG. 6, system 4000 may include a diagnostic imaging system 1000, a treatment planning system 2000 and a radiation treatment delivery system 100.

Diagnostic imaging system 1000 may be any system capable of producing medical diagnostic images of a volume of interest ("VOI") in a patient that may be used for subsequent medical diagnosis, treatment planning and/or treatment delivery. For example, diagnostic imaging system 1000 may be a computed tomography ("CT") system, a magnetic resonance imaging ("MRI") system, a positron emission tomography ("PET") system, an ultrasound system or the like. For ease of discussion, diagnostic imaging system 1000 may be discussed below at times in relation to a CT x-ray imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, can also be used that would be illuminated by each x-ray imaging source. Alternatively, other numbers and configurations of imaging sources and imaging detectors may be used.

The imaging source 1010 and the imaging detector 1020 are coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor ("DSP") or other type of device such as a controller or field programmable gate array ("FPGA"). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network ("LAN") link or a wide area network ("WAN") link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a DSP or other type of device such as a controller or FPGA. Processing device 2010 may be configured to execute instructions for performing treatment planning operations discussed herein.

Treatment planning system 2000 may also include system memory 2020 that may include a random access memory ("RAM"), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory ("ROM") and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube ("CRT") or liquid crystal display ("LCD"), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as radiation treatment delivery system 100, so that it may not be necessary to export from the treatment planning system prior to treatment delivery. Treatment planning system 2000 may be linked to radiation treatment delivery system 100 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or radiation treatment delivery system 100 may be in decentralized locations such that the systems may be physically remote from each other. Alternatively, any of diagnostic imaging system 1000, treatment planning system 2000 and/or radiation treatment delivery system 100 may be integrated with each other in one or more systems.

Radiation treatment delivery system 100 includes a therapeutic and/or surgical radiation source 105 to administer a prescribed radiation dose to a target volume in conformance with a treatment plan. Radiation treatment delivery system 100 may also include an imaging system 3020 (including imaging sources 120 and detectors 115) to capture intra-treatment images of a patient volume (including the target volume) for registration or correlation with the diagnostic images described above in order to position the patient with respect to the radiation source. Radiation treatment delivery system 100 may also include a digital processing system 3030 to control therapeutic radiation source 105, imaging system 3020, and a patient support device such as a treatment couch 110. Digital processing system 3030 may include one or more general-purpose processors (e.g., a microprocessor), special purpose processor such as a DSP or other type of device such as a controller or FPGA. Digital processing system 3030 may also include other components (not shown) such as memory, storage devices, network adapters and the like. Digital processing system 3030 may be coupled to therapeutic radiation source 105, imaging system 3020 and treatment couch 110 by a bus 3045 or other type of control and communication interface.

Figure 7:
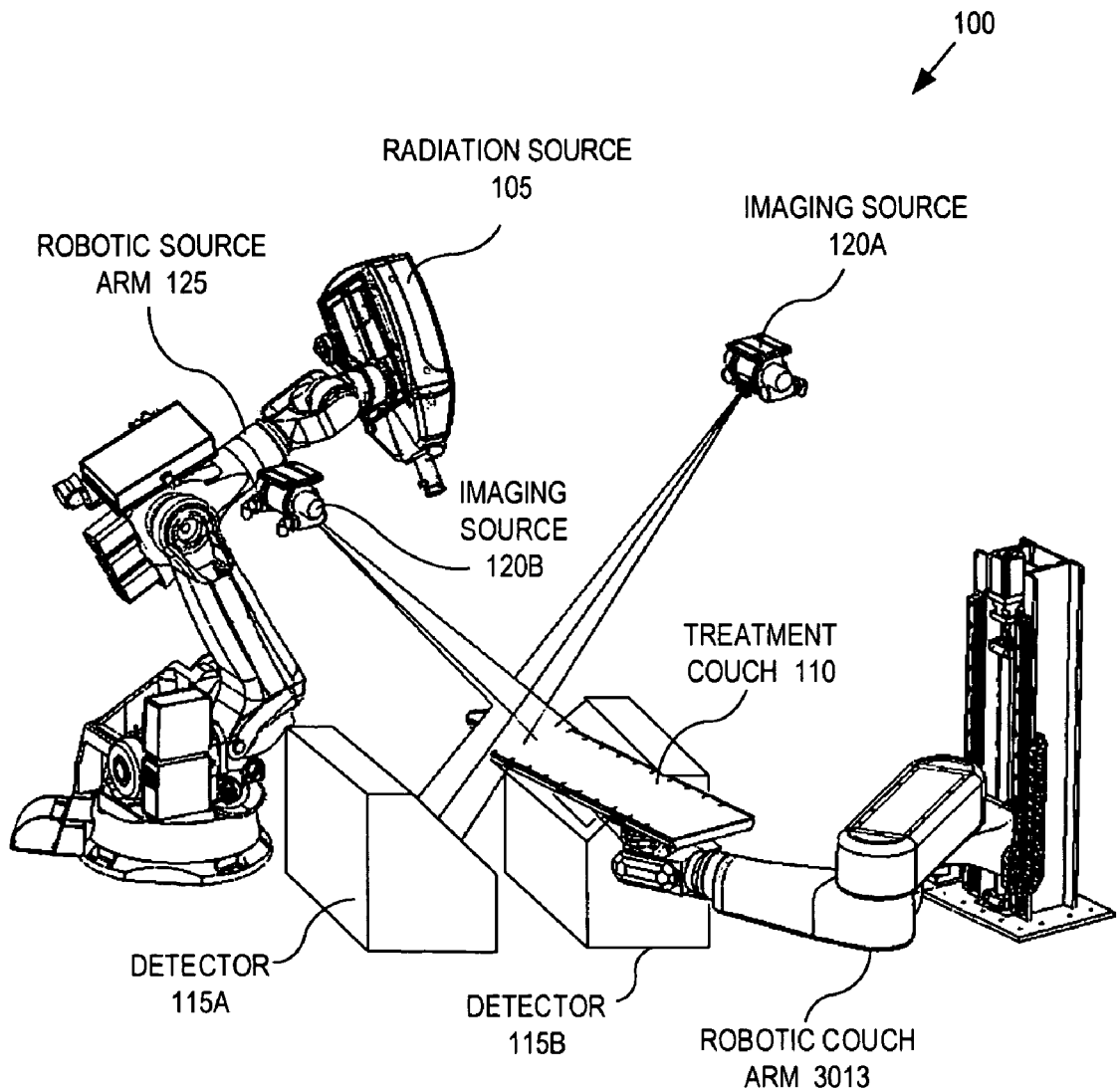
FIG. 7 is a perspective view of a radiation treatment delivery system, in accordance with an embodiment of the invention.

FIG. 7 is a perspective view of a radiation treatment delivery system 100, in accordance with an embodiment of the invention. In one embodiment, radiation treatment delivery system 100 may be an image-guided, robotic-based radiation treatment system (e.g., for performing radiosurgery) such as the CyberKnife® system developed by Accuray, Inc. of California. In FIG. 7, radiation source 105 may be a linear accelerator ("LINAC") mounted on the end of a robotic source arm 125 having multiple (e.g., 5 or more) degrees of freedom in order to position the LINAC to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions (hypo-fractionation) as determined during treatment planning. With radiation treatment delivery system 100, in one embodiment, radiation beams may be delivered according to the treatment plan without fixing the patient to a rigid, external frame to register the intra-operative position of the target volume with the position of the target volume during the pre-operative treatment planning phase.

Imaging system 3020 (see FIG. 7) may be represented by imaging sources 120A and 120B and detectors (imagers) 115A and 115B in FIG. 8. In one embodiment, imaging sources 120A and 120B are X-ray sources. In one embodiment, for example, two imaging sources 120A and 120B may be nominally aligned to project imaging x-ray beams through a patient from two different angular positions (e.g., separated by 90 degrees, 45 degrees, etc.) and aimed through the patient on treatment couch 110 toward respective detectors 115A and 115B. In another embodiment, a single large imager can be used that would be illuminated by each x-ray imaging source. Alternatively, other numbers and configurations of imaging sources and detectors may be used.

Digital processing system 3030 may implement algorithms to register images obtained from imaging system 3020 with pre-operative treatment planning images in order to align the patient on the treatment couch 110 within the radiation treatment delivery system 100, and to precisely position the radiation source 105 with respect to the target volume.

In the illustrated embodiment, treatment couch 110 is coupled to a robotic couch arm 3013 having multiple (e.g., 5 or more) degrees of freedom. Robotic couch arm 3013 may have five rotational degrees of freedom and one substantially vertical, linear degree of freedom. Alternatively, robotic couch arm 3013 may have six rotational degrees of freedom and one substantially vertical, linear degree of freedom or at least four rotational degrees of freedom. Robotic couch arm 3013 may be vertically mounted to a column or wall, or horizontally mounted to pedestal, floor, or ceiling. Alternatively, the treatment couch 110 may be a component of another mechanical mechanism, such as the Axum® treatment couch developed by Accuray, Inc. of California, or be another type of conventional treatment table known to those of ordinary skill in the art. Robotic couch arm 3013 and treatment couch 110 may be referred to as a positioning system for a patient.

Alternatively, radiation treatment delivery system 100 may be another type of treatment delivery system, for example, a gantry based (isocentric) intensity modulated radiotherapy ("IMRT") system. In a gantry based system, a therapeutic radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method, comprising:
generating an optimized treatment plan for delivering a dose of radiation to a volume of interest ("VOI") in a patient using fewer changes to a treatment plan parameter during delivery of the dose of radiation than available to a radiation treatment delivery system, the optimized treatment plan to limit a number of adjustments to the treatment plan parameter during delivery of the dose of radiation;
analyzing the optimized treatment plan to determine whether a quality of the optimized treatment plan is acceptable;
comparing metrics between the optimized treatment plan and a second treatment plan using more changes to the treatment plan parameter during delivery of the dose of radiation than the optimized treatment plan; and
determining whether to treat the VOI with the optimized treatment plan or the second treatment plan based at least in part on comparing the metrics.

2. The method of claim 1, wherein the optimized treatment plan comprises a partial node treatment plan for delivering the dose of radiation to the VOI using a subset of available spatial nodes for positioning a radiation source of the radiation treatment delivery system, the partial node treatment plan to limit the radiation source to visiting only the subset of the available spatial nodes during delivery of the dose of radiation.

3. The method of claim 2, wherein the second treatment plan comprises a complete node treatment plan, the method further comprising:
generating the complete node treatment plan for delivering the dose of radiation to the VOI using a complete set of the available spatial nodes so the radiation source visits all of the available spatial nodes during delivery of the dose of radiation; and
determining projected time savings of the partial node treatment plan versus the complete node treatment plan.

4. The method of claim 3, wherein comparing the metrics between the partial node treatment plan and the complete node treatment plan comprises:
comparing conformality of the dose of radiation to the VOI between the partial node treatment plan and the complete node treatment plan;
comparing homogeneity of the dose of radiation to the VOI between the partial node treatment plan and the complete node treatment plan; and
comparing risk of complications to the patient during delivery of the dose of radiation between the partial node treatment plan and the complete node treatment plan.

5. The method of claim 3, further comprising determining whether to deliver the dose of radiation using the partial node treatment plan or the complete node treatment plan based at least in part on the comparison of the metrics and the projected time savings.

6. The method of claim 5, further comprising:
delivering the dose of radiation to the patient using the partial node treatment plan, if the comparison of the metrics and the projected time savings indicate the partial node treatment plan is advantageous over the complete node treatment plan; else
delivering the dose of radiation to the patient using the complete node treatment plan, if the comparison of the metrics and the projected time savings indicate the partial node treatment plan is not advantageous over the complete node treatment plan.

7. The method of claim 2, wherein analyzing the partial node treatment plan to determine whether the quality of the partial node treatment plan is acceptable comprises:
determining whether conformality of the dose of radiation delivered to the VOI using the partial node treatment plan will fall within an acceptable conformality deviation;
determining whether homogeneity of the dose of radiation delivered to the VOI using the partial node treatment plan will fall within an acceptable homogeneity deviation.

8. The method of claim 7, wherein analyzing the partial node treatment plan to determine whether the quality of the partial node treatment plan is acceptable further comprises determining whether a risk of complications to the patient using to the partial node treatment plan is acceptable.

9. The method of claim 8, wherein determining whether the risk of complications to the patient using the partial node treatment plan is acceptable comprises analyzing proximities between radiation beams delivering the dose of radiation to the VOI pass to critical structures within the patient.

10. The method of claim 2, further comprising:
searching a database of node subsets for generating partial node treatment plans, each of the node subsets having a different subset of the available spatial nodes for positioning the radiation source during treatment of the patient; and
analyzing the node subsets to determine whether any of the node subsets is a candidate for generating the partial node treatment plan.

11. The method of claim 10, wherein the database of node subsets includes at least some of the node subsets indexed to anatomy features.

12. The method of claim 11, wherein the database node subsets includes some of the node subsets tailored for generating partial node treatment plans for treating at least one of a spine lesion, a prostate lesion, and a lung lesion.

13. The method of claim 10, wherein the node subsets comprise a partial collection of the available spatial nodes and known safe paths linking the partial collection of the available spatial nodes for translating the radiation source along.

14. The method of claim 1, wherein the number of adjustments to the treatment plan parameter limited by the optimized treatment plan comprises a first number of adjustments, and further comprising:
generating a complete treatment plan for delivering the dose of radiation to the VOI using a second number of adjustments to the treatment plan parameter during delivery of the dose of radiation, the second number of adjustments greater than the first number of adjustments;
comparing metrics between the optimized treatment plan and the complete treatment plan; and
determining projected time savings of the optimized treatment plan versus the complete treatment plan.

15. The method of claim 14, wherein the radiation treatment delivery system comprises an image guided radiation treatment delivery system, wherein the treatment plan parameter comprises a location of an imaging center of the image guided radiation treatment delivery system, and wherein the optimized treatment plan uses fewer imaging centers to delivery the dose of radiation than the complete treatment plan.

16. The method of claim 14, wherein the treatment plan parameter comprises a treatment couch position of the radiation treatment delivery system and wherein the optimized treatment plan uses fewer treatment couch positions to delivery the dose of radiation than the complete treatment plan.

17. The method of claim 14, wherein the treatment plan parameter comprises a source to axis distance of the radiation treatment delivery system and wherein the optimized treatment plan uses fewer changes to the source to axis distance during delivery of the dose of radiation than the complete treatment plan.

18. A machine-accessible medium that provides instructions that, if executed by a machine, will cause the machine to perform operations comprising:
generating an optimized treatment plan for delivering a dose of radiation to a volume of interest ("VOI") in a patient using fewer changes to a treatment plan parameter during delivery of the dose of radiation than available to a radiation treatment delivery system, the optimized treatment plan to limit a number of adjustments to the treatment plan parameter during delivery of the dose of radiation;
analyzing the optimized treatment plan to determine whether a quality of the optimized treatment plan is acceptable;
comparing metrics between the optimized treatment plan and a second treatment plan using more changes to the treatment plan parameter during delivery of the dose of radiation than the optimized treatment plan; and
determining whether to treat the VOI with the optimized treatment plan or the second treatment plan based at least in part on comparing the metrics.

19. The machine-accessible medium of claim 18, wherein the optimized treatment plan comprises a partial node treatment plan for delivering the dose of radiation to the VOI using a subset of available spatial nodes for positioning a radiation source of the radiation treatment delivery system, the partial node treatment plan to limit the radiation source to visiting only the subset of the available spatial nodes during delivery of the dose of radiation.

20. The machine-accessible medium of claim 19, wherein the second treatment plan comprises a complete node treatment plan, the machine-accessible medium further providing instructions that, if executed by the machine, will cause the machine to perform further operations, comprising:
generating the complete node treatment plan for delivering the dose of radiation to the VOI using a complete set of the available spatial nodes so the radiation source visits all of the available spatial nodes during delivery of the dose of radiation; and
determining projected time savings of the partial node treatment plan versus the complete node treatment plan.

21. The machine-accessible medium of claim 20, wherein comparing the metrics between the partial node treatment plan and the complete node treatment plan comprises:
comparing conformality of the dose of radiation to the VOI between the partial node treatment plan and the complete node treatment plan;
comparing homogeneity of the dose of radiation to the VOI between the partial node treatment plan and the complete node treatment plan; and
comparing risk of complications to the patient during delivery of the dose of radiation between the partial node treatment plan and the complete node treatment plan.

22. The machine-accessible medium of claim 20, further providing instructions that, if executed by the machine, will cause the machine to perform further operations, comprising:
determining whether to deliver the dose of radiation using the partial node treatment plan or the complete node treatment plan based at least in part on the comparison of the metrics and the projected time savings.

23. The machine-accessible medium of claim 19, further providing instructions that, if executed by the machine, will cause the machine to perform further operations, comprising:
searching a database of node subsets for generating partial node treatment plans, each of the node subsets having a different subset of the available spatial nodes for positioning the radiation source during treatment of the patient; and
analyzing the node subsets to determine whether any of the node subsets is a candidate for generating the partial node treatment plan.

24. The machine-accessible medium of claim 23, wherein the database of node subsets includes at least some of the node subsets indexed to anatomy features.

25. The machine-accessible medium of claim 24, wherein the database node subsets includes some of the node subsets tailored for generating partial node treatment plans for treating at least one of a spine lesion, a prostate lesion, and a lung lesion.

26. The machine-accessible medium of claim 18, wherein the number of adjustments to the treatment plan parameter limited by the optimized treatment plan comprises a first number of adjustments, and further comprising:
generating a complete treatment plan for delivering the dose of radiation to the VOI using a second number of adjustments to the treatment plan parameter during delivery of the dose of radiation, the second number of adjustments greater than the first number of adjustments;

comparing metrics between the optimized treatment plan and the complete treatment plan; and determining projected time savings of the optimized treatment plan versus the complete treatment plan.

27. The machine-accessible medium of claim 26, wherein the radiation treatment delivery system comprises an image guided radiation treatment delivery system, wherein the treatment plan parameter comprises a location of an imaging center of the image guided radiation treatment delivery system, and wherein the optimized treatment plan uses fewer imaging centers to delivery the dose of radiation than the complete treatment plan.

28. The machine-accessible medium of claim 26, wherein the treatment plan parameter comprises a treatment couch position of the radiation treatment delivery system and wherein the optimized treatment plan uses fewer treatment couch positions to delivery the dose of radiation than the complete treatment plan.

29. The machine-accessible medium of claim 26, wherein the treatment plan parameter comprises a source to axis distance of the radiation treatment delivery system and wherein the optimized treatment plan uses fewer changes to the source to axis distance during delivery of the dose of radiation than the complete treatment plan.

30. A system, comprising:
  a database storing a library of node subsets for generating partial node treatment plans to deliver a dose of radiation to a volume of interest ("VOI") in a patient and a complete node set for generating a complete node treatment plan, each of the node subsets having a different subset of available spatial nodes for positioning a radiation source during delivery of the dose of radiation, the complete node set including more of the available spatial nodes than any of the node subsets; and
  a processor coupled to the database to access the library of node subsets and to generate the partial node treatment plans and the complete node treatment plan, the processor further coupled to analyze the partial node treatment plans to determine whether a quality of each of the partial node treatment plans is acceptable and to compare metrics between the partial node treatment plans and the complete node treatment plan.

31. The system of claim 30, wherein the complete node set is for generating the complete node treatment plan to deliver the dose of radiation to the VOI using the complete node set by translating the radiation source through all of the available spatial nodes during delivery of the dose of radiation, and wherein the processor is further configured to generate the complete node treatment plan.

32. The system of claim 31, wherein the processor is further configured to compare metrics between the partial node treatment plans and the complete node treatment plan and to determine projected time savings of each of the partial node treatment plans versus the complete node treatment plan.

33. The system of claim 32, wherein the processor is configured to compare conformality of the dose of radiation to the VOI between the partial node treatment plans and the complete node treatment plan, to compare homogeneity of the dose of radiation to the VOI between the partial node treatment plans and the complete node treatment plan, and to compare risk of complications to the patient during delivery of the dose of radiation between the partial node treatment plans and the complete node treatment plan.

34. The system of claim 30, wherein the database stores at least some of the node sets indexed to treatments of anatomy ailments.

35. The system of claim 34, wherein at least some of the node sets are for generating the partial node treatment plans tailored for treating at least one of spine lesion, a prostate lesion, and a lung lesion.

36. An apparatus, comprising:
  means for generating an optimized treatment plan for delivering a dose of radiation to a volume of interest ("VOI") in a patient using fewer changes to a treatment plan parameter during delivery of the dose of radiation than available to a radiation treatment delivery system, the optimized treatment plan to limit a number of adjustments to the treatment plan parameter during delivery of the dose of radiation;
  means for analyzing the optimized treatment plan to determine whether a quality of the optimized treatment plan is acceptable;
  means for comparing metrics between the optimized treatment plan and a second treatment plan using more changes to the treatment plan parameter during delivery of the dose of radiation than the optimized treatment plan; and
  means for determining whether to treat the VOI with the optimized treatment plan or the second treatment plan based at least in part on comparing the metrics.

37. The apparatus of claim 36, wherein the optimized treatment plan comprises a partial node treatment plan for delivering the dose of radiation to the VOI using a subset of available spatial nodes for positioning a radiation source of the radiation treatment delivery system, the partial node treatment plan to limit the radiation source to visiting only the subset of the available spatial nodes during delivery of the dose of radiation.

38. The apparatus of claim 37, wherein the second treatment plan comprises a complete node treatment plan, the apparatus further comprising:
  means for generating the complete node treatment plan for delivering the dose of radiation to the VOI using a complete set of the available spatial nodes so the radiation source visits all of the available spatial nodes during delivery of the dose of radiation; and
  means for determining projected time savings of the partial node treatment plan versus the complete node treatment plan.

39. The apparatus of claim 38, wherein the means for comparing the metrics between the partial node treatment plan and the complete node treatment plan includes:
  means for comparing conformality of the dose of radiation to the VOI between the partial node treatment plan and the complete node treatment plan;
  means for comparing homogeneity of the dose of radiation to the VOI between the partial node treatment plan and the complete node treatment plan; and
  means for comparing risk of complications to the patient during delivery of the dose of radiation between the partial node treatment plan and the complete node treatment plan.

40. The apparatus of claim 37, further comprising:
  means for searching a database of node subsets for generating partial node treatment plans, each of the node subsets having a different subset of the available spatial nodes for positioning the radiation source during treatment of the patient; and means for analyzing the node subsets to determine whether any of the node subsets is a candidate for generating the partial node treatment plan.

41. The apparatus of claim 40, wherein the database of node subsets includes at least some of the node subsets indexed to anatomy features.

42. The apparatus of claim 41, wherein the database node subsets includes some of the node subsets tailored for generating partial node treatment plans for treating at least one of a spine lesion, a prostate lesion, and a lung lesion.

43. The apparatus of claim 36 wherein the number of adjustments to the treatment plan parameter limited by the optimized treatment plan comprises a first number of adjustments, and further comprising:
    means for generating a complete treatment plan for delivering the dose of radiation to the VOI using a second number of adjustments to the treatment plan parameter during delivery of the dose of radiation, the second number of adjustments greater than the first number of adjustments;
    means for comparing metrics between the optimized treatment plan and the complete treatment plan; and
    means for determining projected time savings of the optimized treatment plan versus the complete treatment plan.

44. The apparatus of claim 43 wherein the radiation treatment delivery system comprises an image guided radiation treatment delivery system, wherein the treatment plan parameter comprises a location of an imaging center of the image guided radiation treatment delivery system, and wherein the optimized treatment plan uses fewer imaging centers to delivery the dose of radiation than the complete treatment plan.

45. The apparatus of claim 43 wherein the treatment plan parameter comprises a treatment couch position of the radiation treatment delivery system and wherein the optimized treatment plan uses fewer treatment couch positions to delivery the dose of radiation than the complete treatment plan.

46. The apparatus of claim 43 wherein the treatment plan parameter comprises a source to axis distance of the radiation treatment delivery system and wherein the optimized treatment plan uses fewer changes to the source to axis distance during delivery of the dose of radiation than the complete treatment plan.

* * * * *